US00PP36817P3

(12) United States Plant Patent
Olesen

(10) Patent No.: US PP36,817 P3
(45) Date of Patent: Jul. 15, 2025

(54) MINIATURE ROSE PLANT NAMED 'Poulpah121'

(50) Latin Name: *Rosa hybrida*
Varietal Denomination: Poulpah121

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/445,474

(22) Filed: Sep. 8, 2023

(65) Prior Publication Data

US 2024/0107913 P1 Mar. 28, 2024

(30) Foreign Application Priority Data

Sep. 30, 2022 (QZ) ..... PBR 2022/2168

(51) Int. Cl.
*A01H 5/02* (2018.01)
*A01H 6/74* (2018.01)

(52) U.S. Cl.
USPC ..... Plt./116
CPC ..... *A01H 6/749* (2018.05)

(58) Field of Classification Search
USPC ..... Plt./116, 123
CPC . A01H 5/02; A01H 5/00; A01H 6/749; A01H 6/74
See application file for complete search history.

(56) References Cited

U.S. PATENT DOCUMENTS

PP28,226 P3 * 8/2017 Olesen ..... Plt./143

OTHER PUBLICATIONS

CPVO 4.20.10 for *Rosa* Poulpah121 retrieved on Oct. 3, 2024 at https://online.plantvarieties.eu/publicConsultationDetails?registerId=20222168&denomination=poulpah121, 2 pp. (Year: 2024).*

* cited by examiner

*Primary Examiner* — June Hwu

(57) ABSTRACT

A new garden rose plant of the Miniature class which has abundant, yellow and red striped flowers and attractive foliage. This new and distinct variety has shown to be uniform and stable in the resulting generations from asexual propagation.

1 Drawing Sheet

Botanical designation: *Rosa hybrida.*
Variety denomination: 'Poulpah121'.

This application claims priority to Plant Breeder's Rights Application Number 2022/2168, which was filed at the Community Plant Variety Rights Office in the European Union on Sep. 30, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2015 and the resulting seeds were planted in a controlled environment in Fredensborg, Denmark. The new variety, named 'Poulpah121', originated as a single seedling from the stated cross.

The new variety may be distinguished from its male pollen parent and female seed parent primarily by the following characteristics. The male pollen parent plant has yellow flowers while the new variety has yellow and red striped flowers. The female seed parent plant has red and pink striped flowers while the new variety has yellow and red striped flowers.

The objective of the hybridization of this rose variety was to create a new and distinct variety with unique qualities, such as:

1. Uniform and abundant yellow and red striped flowers;
2. Vigorous, but compact growth when propagated on its own roots;
3. Exceptional disease resistance.

This combination of qualities is not present in previously available commercial cultivars of this type, known to the inventor, and distinguish 'Poulpah121' from all other varieties of which we are aware.

As part of the rose development program, Mogens N. Olesen germinated the seeds from the aforementioned hybridization during winter of 2015 and conducted evaluations on the resulting seedlings in a controlled environment in Fredensborg, Denmark. 'Poulpah121' was selected in the spring of 2016 by the inventor as a single plant from the progeny of the aforementioned hybridization.

Asexual reproduction of 'Poulpah121' by rooted cuttings was first done by Mogens N. Olesen in the nursery in Fredensborg, Denmark in July, 2016. This initial and other subsequent asexual propagations conducted in controlled environments have demonstrated that the characteristics of 'Poulpah121' are true to type and are transmitted from one generation to the next.

DESCRIPTION OF THE DRAWING

The accompanying color illustration show as true as is reasonably possible to obtain in color photographs of this type, the typical characteristics of the buds, flowers, leaves, and stems, of 'Poulpah121'.

Specifically illustrated in the drawing is an open flower viewed from above, a cluster of flower buds and open flower viewed from the side, sepals detached revealing reproductive flower parts, petals detached, a flower bud, bare stem, and mature leaves. Plants shown are 5 months of age.

DETAILED DESCRIPTION OF THE VARIETY

The following is a description of 'Poulpah121', as observed in its growth in an indoor glasshouse nursery in Odense Denmark. Observed plants are 5 months of age, and were grown on their own roots in 19 cm pots. Color references are made using The Royal Horticultural Society (London, England) Colour Chart, 2001, except where common terms of color are used.

For a comparison, several physical characteristics of the rose variety 'Poulpal061', U.S. Plant Pat. No. 28,226 are compared to the claimed plant. The upper surface of outer petals of 'Poulpah121' have the coloration described as streaks of Yellow Group 13A and Red Group 39B. Basal zone Yellow Group 13A. The coloration of the outer petals, upper surface, of 'Poulpal061' are Red Group 43A at marginal zone, Red Group 41B at middle zone splashed with White Group 155C. On the flower reproductive parts, the filaments of the claimed plant are Yellow-Orange Group 14B with intonations of Orange-Red Group N34D, while filaments of 'Poulpal061' are Yellow 7B. In terms of growth height, 'Poulpal061' is about 80 cm tall, while 'Poulpah121' is 40 cm tall.

FLOWER AND FLOWER BUD

Blooming habit: Continuous.

Flower bud:

- *Size*.—Upon opening, 29 mm in length from base of receptacle to end of bud. Bud diameter is 16 mm.
- *Bud form*.—Ovoid.
- *Bud color*.—As sepals divide petals are Yellow Group 12A and Orange-Red Group 32A.
- *Sepal inner surface*.—Color: Yellow-Green Group 146D. Surface: Lightly pubescent.
- *Sepal outer surface*.—Color: Yellow-Green Group 144A. Texture: Smooth.
- *Sepal shape*.—Apex: Cirrhose. Base: Flat at union with receptacle.
- *Sepal margin*.—Margins have very weak foliaceous appendages on three of the five sepals.
- *Sepal size*.—About 24 mm long, 5 mm wide.
- *Receptacle*.—Texture: Smooth. Size: 8 mm in height, 6 mm wide. Color: Yellow-Green Group 144A. Shape: Campanulate.
- *Pedicel*.—Surface: Smooth. Length: 54 mm. Diameter: 2 mm on average. Color: Yellow-Green Group 144A. Strength: Strong.
- *Peduncle*.—Length: 3 to 4 cm. Diameter: About 3 mm. Color: Yellow-Green Group 145A. Texture: Smooth.

Flower bud development: Flower buds are borne single and in clusters of 3 to 5 flower buds per stem. Development as a panicle.

Flower bloom:

- *Fragrance*.—Moderate to light floral.
- *Duration*.—The blooms have a duration on the plant of approximately 21 days. Petals fall cleanly away from plant after flowers have fully matured.
- *Size*.—Flower diameter is 70 mm when open. Flower depth is 30 mm.
- *Flower shape*.—High centered, double, with a high pointed center which is tightly closed.
- *Shape of flower, side view*.—The upper portion is convex. The lower portions flat concave.

Petalage: Under normal conditions, flowers have about 38 petals.

General tonality of flower: Open flowers are distinctly Yellow Group 14D and Red Group 52C.

Petal color:

- *Upon opening, outer petals*.—Upper surface: Streaks of Yellow Group 13A and Red Group 39B. Lower surface: Red Group 38A with shades of Orange Group 24C. Shades of Yellow Group 13C at basal zone about 5 mm in length. Streaks of Yellow Group 13D.
- *Upon opening, inner petals*.—Upper surface: At the basal zone Yellow Group 13A extending approximately 5 mm from the petal base. At the marginal zone Red Group 43B. Lower surface: Generally Orange-Red Group 33C. At the marginal zone Red Group 41C. At the basal zone distinctly Yellow Group 13A about 5 mm from the petal base.
- *After opening, outer petals*.—Upper surface: Yellow Group 4C with streaks of Red-Purple Group 62A. Yellow Group 13C at the basal zone about 5 mm from the petal base. Lower surface: Yellow Group 4C with streaks of Red-Purple Group 62A. Yellow Group 13C at the basal zone about 5 mm from the petal base.
- *After opening, inner petals*.—Upper surface: Generally Yellow Group 10B with streaks of Red Group 37B. Distinct Basal zone coloration Yellow Group 12A about 5 mm from the petal base. Lower surface: Yellow Group 10B with streaks of Red Group 37B. Basal zone Yellow Group 12A about 5 mm from the petal base.

Petals:

- *Petal reflex*.—Slightly reflexed.
- *Margin*.—Entire with a slight point at the apex. Occasionally small clefts. No undulations.
- *Shape*.—Broad and elliptic. Apex shape: Rounded. Base shape: Acute.
- *Size*.—36 mm (l)×37 mm (w).
- *Texture*.—Smooth at the upper and lower surface.
- *Thickness*.—Average.

Petaloids:

- *Size*.—14 mm (l) by 9 mm (w).
- *Quantity*.—About 3.
- *Shape*.—Elliptical with an acute base and acute apex.
- *Color*.—On upper and lower surfaces petaloids are Yellow Group 10B with streaks of Red Group 37B. Petaloid spot at the basal zone is Yellow Group 12A.

Reproductive flower parts:

- *Pollen*.—None observed.
- *Anthers*.—Size: 3 mm in length. Color: Yellow Group 12B. Quantity: 32 on average.
- *Filaments*.—Color: Yellow-Orange Group 14B with intonations of Orange-Red Group N34D. Length: 4 mm.

*Pistils*.—Length: 7 mm. Quantity: 27 on average.
*Stigmas*.—Color: Orange-White Group 159A.
*Styles*.—Color: Red Group 53C.
*Location of stigmas*.—Level in location relative to the length of the filaments and the height of the anthers.
*Hips*.—None Observed.

PLANT

Plant growth: Upright. Plants are about 40 cm in height, and 22 cm wide.
Stems:
*Color of juvenile growth*.—Yellow-Green Group 144B, with moderate to strong intonations of Greyed-Purple 187B.
*Color of mature growth*.—Yellow-Green Group 144A.
*Length*.—Canes are about 17 cm from the base of the plant to the flowering portion.
*Diameter*.—About 3 to 4 mm.
*Internodes*.—On mature canes about 40 mm between nodes.
*Surface texture*.—Young wood: Smooth. Older wood: Smooth.
Long prickles:
*Incidence*.—1 prickles per 10 cm of stem.
*Size*.—Average length of prickles on mature stems is 4 mm.
*Shape*.—Upper and lower portion are linear.
*Color*.—Juvenile prickles: Greyed-Red Group 180A. Mature prickles: Greyed-Red Group 180A.
Plant foliage:
*Compound leaf*.—About 155 mm (l)×110 (w).
*Quantity*.—2 leaves per 10 cm of stem on average.
*Leaf bearing angle to the stem*.—45 degrees.
*Color of juvenile foliage*.—Upper side: Yellow-Green Group 144A. Lower side: Yellow-Green Group 144B.
*Color of mature foliage*.—Upper side: Yellow-Green Group 147A. Lower side: Yellow-Green Group 146A.
Plant leaves and leaflets:
*Stipules*.—Size: 18 mm long, 3 mm wide. Quantity: 2 per compound leaf. Shape: Linear, slightly broad based with strong appendages. Margins: Finely serrated. Color: Yellow-Green Group 144A on the upper and lower surface.
*Petiole*.—Length: 30 to 15 mm. Diameter: 2 mm. Upper surface color: Yellow-Green Group 144A. Lower surface color: Yellow-Green Group 144A. Surface Texture: The upper and lower surfaces are smooth.
*Rachis*.—Length: About 65 mm. Upper surface color: Yellow-Green Group 144A. Lower surface color: Yellow-Green Group 144A. Surface Texture: The upper surface is smooth. The lower surface has small prickles.
*Leaflet*.—Quantity: Normally 5 sometimes 7 leaflets. Margins: Serrated. Undulations of margin are absent or very weak. Size: Terminal leaflets are about 66 mm long, 44 mm wide. Shape: Generally elliptical. Base: Rounded. Apex: Acute or mucronate. Texture: The upper and lower portion are smooth. Thickness: Average. Arrangement: Odd pinnate. Venation: Reticulate. Glossiness: Moderately glossy on the upper surface. The lower surface is not glossy.
Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.
Cold hardiness: The variety is tolerant to USDA Cold Hardiness Zone 6.
Heat tolerance: The variety has been found to be suitable for climate conditions found in the American Horticulture Society heat zone 7.

I claim:

1. A new and distinct variety of rose plant named 'Poulpah121' substantially as described and illustrated herein.

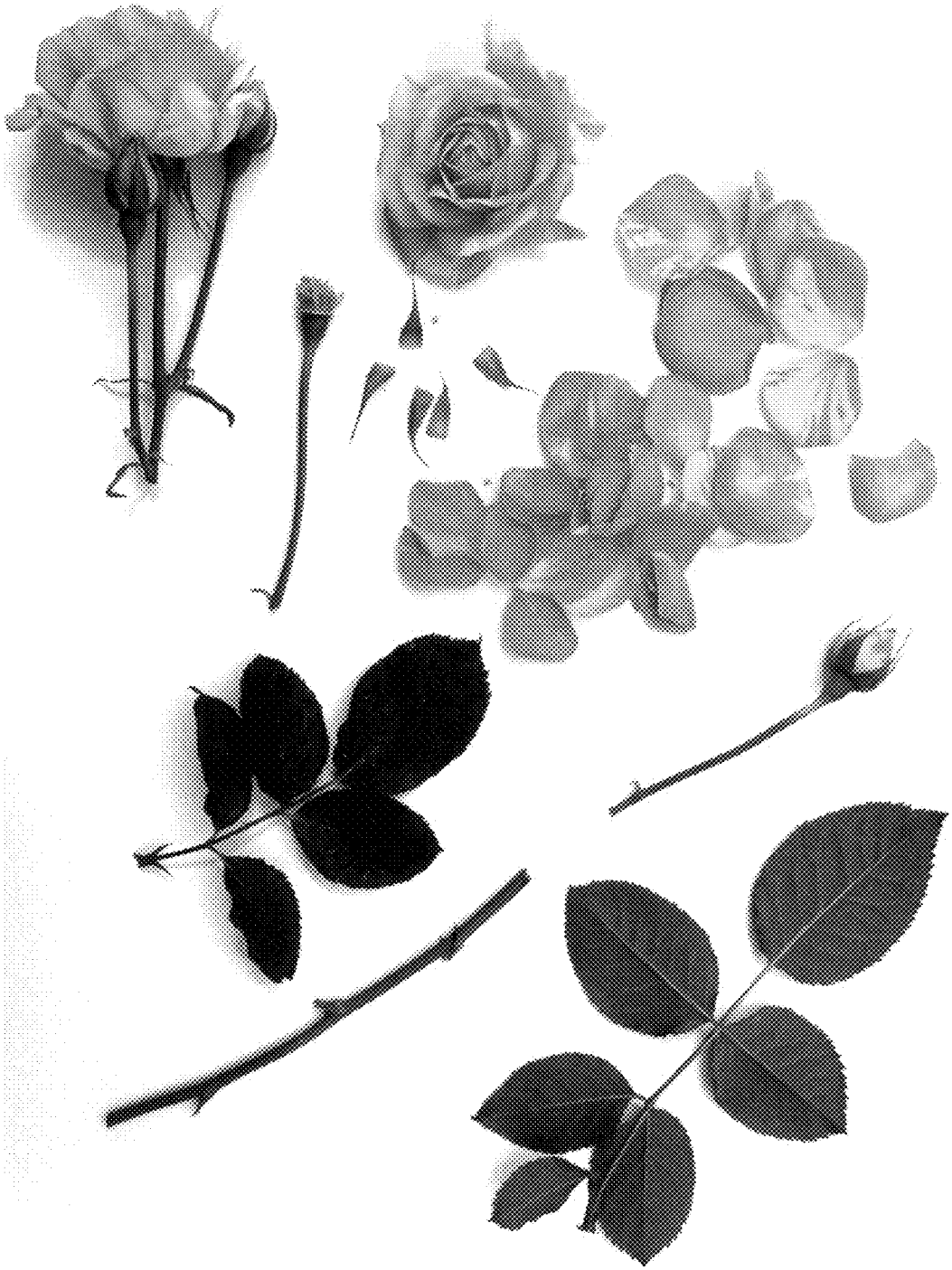

* * * * *